US00PP15080P3

(12) United States Plant Patent
Dhyani et al.

(10) Patent No.: US PP15,080 P2
(45) Date of Patent: Aug. 17, 2004

(54) GLADIOLUS HYBRID PLANT 'PALAMPUR DELIGHT'

(50) Latin Name: *Gladiolus hybrid*
Varietal Denomination: Palampur Delight

(75) Inventors: Devendra Dhyani, Palampur (IN); Debasish Mukherjee, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/106,150

(22) Filed: Mar. 25, 2002

(65) Prior Publication Data

US 2003/0182701 P1 Sep. 25, 2003

(51) Int. Cl.[7] ..... A01H 5/00

(52) U.S. Cl. ..... Plt./301

(58) Field of Search ..... Plt./301

*Primary Examiner*—Bruce R. Campell
*Assistant Examiner*—Michelle Kizilkaya
(74) *Attorney, Agent, or Firm*—Merchant & Gould P.C.

(57) ABSTRACT

The present invention relates to a novel hybrid plant named 'Palampur Delight' and belonging to the family Iridaceae said plant is a cross between two gladiolus varieties, 'Her Majesty' and 'Eurovision' and is an ornamental plant widely cultivated for beautiful flowers which are of commercial and export value, further said plant is propagated vegetatively by corms and hence can be maintained as a stable genotype.

1 Drawing Sheet

GENUS AND SPECIES OF THE PLANT CLAIMED AND VARIETY DENOMINATION

The present invention relates to a novel Gladiolus hybrid sp. variety named 'Palampur Delight'. This new variety belongs to the family Iridaceae, genus Gladiolus L., and species Gladiolus sp. (Gladiolus hybrid). The novel plant being a hyrbid, has been developed in a breeding programme. The novel plant 'Palampur Delight' is propagated vegetatively by corms and hence can be maintained as a stable genotype. The plant of the invention is a cross between two gladiolus varieties, 'Her Majesty' (unpatented) and 'Eurovision' (unpatented) and is an ornamental plant widely cultivated for beautiful flowers which are of commercial and export value.

BACKGROUND OF THE INVENTION

Gladiolus is a herbaceous bulbous plant grown for its beautiful flowers of different colour, shades and shapes throughout the world. Gladiolus belongs to the Family Iridaceae, Order Liliales and Class Monocotyledon.

Gladiolus is one of the important cut flowers throughout the world. The commercial cultivation is wide spread in temperate, tropical and subtropical climates. The demand of new varieties with better colour, quality flowers, and planting materials is always existing in the floriculture trade.

The modern garden cultivators gladiolus come from diverse genetic parentages. It has cumulative heterozygosity for many characters inherent with complex genetic constitution. In gladiolus, diverse parents are crossed together and the cultivars and the species that differ widely in chromosome numbers are also cross-fertile. In the present invention, the desirable strains obtained in $F_1$ generation were perpetuated vegetatively without being segregated in the following generations, so that the cultivars which are available today may be $F_2$, $F_3$ to $F_8$ or so of a particular cross further blended with some extra parents at nearly every generation. Thus they are not allowed to segregate freely in further generations because it is desirable to grow the plants asexually. Because of this reason, now the available modern cultivars have become so complex that the offspring obtained by crossing them, even two seedlings, do not appear similar [(Misra, 1975) Gladiolus Br. Assn. Newsletter, No.12, pp. 2–5].

The Applicants collected germplasm of different cultivars and hybrid varieties of gladiolus from National Botanical Research Institute Lucknow, India as per the list of gladiolus cultivars grown in India and described in the bulletin of 'gladiolus' Economic Botany Information Service by Sharma et al. published by the Director National Botanical Research Institute Lucknow, 1988. Germplasm of gladiolus was also collected from Netherlands in 1991 and various nurseries of Kalimpong, Darjeeling, West Bengal, India. The record of the collected germplasm of gladiolus was maintained in the accession register of the Floriculture Division of the Institute of Himalayan Bioresource Technology (IHBT), Palampur, India.

The applicants initiated a breeding program to develop better types of gladiolus hybrids suitable to wide range of climatic conditions, and having wide range of characteristics such as better colour, increased number of florets and spike length as per the international standards, better yield of corms and cormels, tolerant to the common diseases etc. The collected germplasm of gladiolus was planted in the experimental field of IHBT for their propagation and multiplication. In this breeding programme conventional breeding method (hybridization) was used. More than 100 cross combinations were made by using distinct varieties such as 'Oscar' (unpatented), 'Jester' (unpatented), 'Snow Princess' (unpatented), 'Eurovision' (unpatented), 'Ballerina' (unpatented), 'King Liar' (unpatented), 'Cherry Blossom' (unpatented), 'Her Majesty' (unpatented), 'Green woodpecker' (unpatented), 'Friendship' (unpatented), 'Vink's Glory' (unpatented), 'Aldebaran' (unpatented), 'Red Beauty'

(unpatented), 'Top Brass' (unpatented), 'Copper King' (unpatented), 'Bonfire' (unpatented), 'White Goddess' (unpatented), 'Sunny Boy' (unpatented), 'Tropic Sea' (unpatented) and 'Friendship Pink' (unpatented), etc.

Color description of some of the parentage as described in NAGC Bulletin.

'Oscar'—Turkey red, throat blotched sulphur yellow.

'Green Woodpecker'—Pea Green, throat blotched pea green spotted ruby red.

'Eurovision'—Signal red, throat streaked pea green.

'Friendship Pink'—Dawn Pink, throat blotched pea green having splashes ruby red.

'Aldebaran'—Straw Yellow and throat bloched signal red.

'Friendship'—Clear pink with yellow throat.

'Jester'—Ruffled, deep Yellow petals and bright red blotches.

'Her Majesty'—Ruffled, Blue violet with darker edges and white throat.

'Snow Princess'—White.

'Eurovision'—Light Vermillion with white veins.

'Purple King'—Purple, rich in colour with white picottee edges, white marks deeper in the throat.

These parentage plants are grown in India for more than 25 years. Details regarding these plants have been published and these plants are available to the public.

As the aim is the production of seed of known parentage, emasculation in first three flowers in a selected spike is done before the opening of the flowers and stigma becomes receptive. Anthers are removed carefully from each flower. Emasculated flowers were covered with butter paper bags used for breeding purposes. Pollination was done in the emasculated flowers next day morning with in 24–30 hours with the pollens of the desired parents in the month of April–May 1991. The seeds were collected from mature pods in the month of August–September and were sown in beds under open field conditions and covered with dry grasses for moisture preservation in December 1991. The resultant seedlings were space planted in the field at Palampur in March–April 1992.

Many seedlings came out from a single cross combination. These plants were critically evaluated and tagged as per the desired colour combinations, growth and flowering parameters. The corn and cormels of the selected hybrid plants were replanted continuously four years in the filed for further evaluation and multiplications. Based on the superior performance for attractive colour combination, compactness of flower spike, number of flowers per spike, length of flower spike, Number of corm and cormels per plant evaluation and selection of superior quality hybrids were made.

Thus, the breeding program involved hybridisation of commonly available gladiolus plants. In other words, the hybrids were developed by crossing parental genotypes involving sexual hybridization in the breeding programme.

The program yielded a number of hybrid plants out of which one genotype namely IHBT-GH-164 was selected and christened as 'Palampur Delight'. The plant is a hybrid between 'Her Majesty' and 'Eurovision'. This plant was found to have new colour, flower size, number of florets per spikes, length of flower spikes, better yield of corm and cormels and less prone to common diseases. Growing the plant on a commercial scale offers the horticulturists an improved and new variety, which can be commercially cultivated.

OBJECTS OF THE INVENTION

The object of the present invention is to provide a new gladiolus genotype christened as 'Palampur Delight'.

SUMMARY OF THE INVENTION

The present invention relates to a novel hybrid plant named 'Palampur Delight' and belonging to the family Iridaceae. The novel plant being a hybrid, has been developed in a breeding programme. The novel plant 'Palampur Delight' is propagated vegetatively by corms and hence can be maintained as a stable genotype. The plant of the invention is a cross between two gladiolus varieties, 'Her Majesty' and 'Eurovision' and is an ornamental plant widely cultivated for beautiful flowers which are of commercial and export value.

BRIEF DESCRIPTION OF THE ACCOMPANYING DRAWING

FIG. 1 is a photograph of field grown flower spike of IHBT-GH-164 ('Palampur Delight') depicting decorative type flowers of Rose Purple (RHS-75D) with Fuchsia Purple (RHS-67A) colour at the edges of the petals and Greenish White (RHS-157D) lip petal. The illustrated flower spike is from a generation of the variety grown in 1992. The plant giving rise to this flower spike was grown under open field conditions in Palampur area of Himachal Pradesh. Palampur is at 1300 m above main sea level, which comes under sub-humid, sub-temperate zone and having average maximum and minimum temperature of 30° C. and 10° C., respectively. The average annual rainfall is approximately 250 cm.

DETAILED BOTANICAL DESCRIPTION

Thus, the invention provides a new genotype christened as 'Palampur Delight'. This plant has been developed through planned breeding experiments conducted at Institute of Himalayan Resources, (IHBT) Palampur, Himachal Pradesh, India with defined aim to develop superior gladiolus genotypes. For this purpose, gladiolus varieties were collected from different sources and grown in the fields at Palampur, India for facilitating breeding program. The emasculation and pollination in different varieties were carried out during the months of April–May 1992. The seeds were collected in July–August 1992 and sown in beds under open field conditions and covered with dry grasses in December 1992. The resultant seedlings were space planted in the field at Palampur in March–April 1993. The corms and cormels of surviving hybrid plants were replanted continuously four years for screening and multiplication.

Based on the superior performance for attractive colour combination, compactness of flower spikes, number of flowers per spikes, length of flower spikes, number of flowers remaining open at a time, number of corm and cormel production per plant, the plant of this invention (IHBT-GH-164) was selected for further observation and evaluation.

Considering the superior characteristics like excellent colour, number of flowers, compactness of flower spikes, plant height, ruffled-ness of flower petals, regeneration potential and freedom from common diseases, it was asexually reproduced through corm and cormels to maintain purity.

The selected hybrid IHBT-GH-164 was christened as 'Palampur Delight' and grown at row distance of 30 cm and plant to plant distance of 15 cm for four consecutive years to study its growth and flowering performance and multiplication. Data were recorded on randomly selected twenty plants every year. The hybrid IHBT-GH-164 maintained uniformity in its growth and flowering performance.

Evidence of Uniformity and Stability

The hybrid IHBT-GH-164 has remained stable and uniform for its morphological characters and showed consistency in performance for various growth and flowering parameters during its evaluation and vegetative multiplication since 1993. Throughout the evaluation period of IHBT-GH-164 no variants were found from the normal population.

The genotype IHBT-GH-164 possesses standard bi color decorative type flowers of Rose Purple (RHS-75D) with Fuchsia Purple (RHS-67A) colour at the edges of the petals. The lip petal is Greenish White (RHS-157D). The flower petals are thick and ruffled which is quite clear from FIG. 1.

The genotype IHBT-GH-164 is distinct in regeneration potential.

The plant of invention 'Palampur Delight' is thus a new and distinct hybrid plant, having the following combination of characters:

(a) Type: Standard.
(b) Days to flower: 85.5 days.
(c) Number of spikes/plant: 1.68.
(d) Length of the flower spike: 125 cm.
(e) Number of flowers/spike: 16.4.
(f) Flower colour: Bi-colour, Rose Purple (RHS-75D) with Fuchsia Purple (RHS-67A) colour on petal's edges. Lip petal Greenish White (RHS-157D).
(g) Type of petals: Petals thick and ruffled.
(h) Number of flowers remains open at a time: 6.51.
(i) Longevity of the $1^{st}$ flower: 2.86 days.
(j) Diameter of $1^{st}$ flower: 12.1 cm.
(k) Longevity of the spike: 8.56 days.
(l) Number of corms/plant: 1.83.
(m) Diameter of corms: 6.04 cm.
(n) Number of cormels/plant: 96.5.

Objective Description of the Genotype 'Palampur Delight'

The following is an objective description of the new variety:

1. Genus: Gladiolus.
2. Species: Hybrid sp.
3. Family: Iridacae.
4. Order: Liliales.
5. Class: Monocotyledon.
6. Common name: Gladiolus/Sword Lily.
7. Plant height: 143.5 cm.
8. Growth habit: Erect, uniform.
9. Stem diameter: 1.21 cm.
10. Number of leaves/plant: 7.36.
11. Height of leaves: 60.3 cm.
12. First flowering: 85.5 days.
13. Type of flowers: Standard.
14. Number of spikes/plant: 1.68.
15. Length of the flower spike: 125 cm.
16. Number of flowers/spike: 16.4.
17. Flower colour: Bi-colour, Rose Purple (RHS-75D) with Fuchsia Purple (RHS-67A) colour on petal's edges. Lip petal Greenish White (RHS-157D).
18. Type of petals: Petals thick and ruffled.
19. Number of flowers remains open at a time: 6.51.
20. Longevity of the $1^{st}$ flower: 2.86 days.
21. Diameter of $1^{st}$ flower: 12.1 cm.
22. Longevity of the spike: 8.56 days.
23. Number of corms/plant: 1.83.
24. Diameter of corms: 6.04 cm.
25. Number of cormels/plant: 96.5.
26. Growing conditions: The plants are grown at open sunny sites and can be grown in a wide variety of soils. However, they require deep, well-drained sandy loam soils having pH around 6.0 to 7.0 for proper growth and flowering.
27. Temperatures: The day temperature could be between 15° C. to 20° C.
28. Leaves: In a mature plant, leaves are attached to the stem in opposite fashion and have dark green color.
29. Number of leaves: 5 to 9.
30. Shape of the leaves: The leaves are sword-shaped phyllode, clustering at the swollen stem base, equivalent in 2-ranks, prominently ribbed, radical and cauline.
31. Description of reproductive parts: Flowers 2-whorled with six perianth segments, attached to a funnel-shaped cup shaping into a bent floraltube, hermaphrodite, trimerous, irregular, medianly zygomorphic, sessile and often protandrous and epigynous, born to one side on a simple or branched inflorescence subtended by two lanceolate, leaf-like valves. The flower is somewhat tubular and possesses six, coloured perianth segments (sepals and petals together), arranged in two whorls. The inflorescence is a spike, with the flowers arranged on the central axis in a single or two rowed symmetrical display, progressing from base to tip. Stamens 3, placed opposite to the outer whorl of the petals, extrose, epiphyllous, inserted below throat, bithecous, dehiscing by vertical slits, filaments distinct and basifixed. Gynoecium tricarpellary and syncarpous, having inferior ovary with axile placementation; style long, slender and simple with typically hinge-like creased trifid stigma and petaloid.
32. Fruits and seeds: Fruits oblong-ellipsoid to obtusely triangular, loculicidal capsule with 3 chambers each having 2 rows mostly with winged seeds.
33. Fragrance: No Fragrance.
34. Mode of reproduction: Vegetatively by corms and cormels.

The variety 'Palampur Delight' can be characterized by its stem color. The colour of the exposed inter node below the first flower bud is closest to Scheele's green (RHS-143 C). The rest of the stem covered with leave sheath is RHS-145 B.

The variety 'Palampur Delight' can be characterized by its leaves. Its leaves are numerous, cauline, alternately overlapped, and sheathed. Its blades are linear, lanceolate, flattened, sword shaped, length 39.5–88.5 cm (average 70.43 cm), width 2.5 cm–4.3 cm (average 3.55 cm), narrow at the base, apex mostly acuminate, rarely acute, margin entire, raised, and fibrous. Its venation is parallel, ribs white-green, fibrous, both surfaces glabrous, scabrid due to fibrous venation, with colour green (RHS-137B).

The variety 'Palampur Delight' can be characterized by its perianth. Its perianth is petaloid. The perianth segment includes 6 tepals (3+3) arranged in two whorls, polyphyllous, shortly stalked, cuneate at the base, apex obtuse, elliptic, oblong, oblanceolate, margin oblique, 3.5–5×6–7.5 cm, and imbricate aestivation.

The variety 'Palampur Delight' can be characterized by its bud size and colour. The colour of flower bud is Fuchsia Purple with Magenta edges (RHS-67D with 66 A). The buds are 6.30 cm to 8.10 cm long (bottom 3 buds were taken) and the average size is 7.16 cm long. The diameter of the lower 3 buds ranging from 0.93 cm to 1.48 cm and the average of 20 buds is 1.16 cm.

The variety 'Palampur Delight' can be characterized by its reproduction organs. For example its androecium includes 3 stamens, which are triandrous, epiphyllous, shorter than the tepals, and arranged in a whorl. Its filaments are white shining, about 3.5 cm long, with anthers bilobed or dithecous, 1.0–1.2 cm long, black-white coloured, extrose, and basifixed.

The variety 'Palampur Delight' can be characterized by its gynoecium. Its ovary is tricarpellary, syncarpus, trilocular, inferior, with many ovules in each locule, and axile placentation. Its style is simple, terminal, equivalent to stamens, about 7 cm long, stigma 3-lobed, petaloid, each lobe folded, wavy, white turning light violet, and with lobes about 5 mm long.

The variety 'Palampur Delight' can be characterized by its plant disease resistance and susceptibility. Some incidence of Fusarium rot was noticed in the field as well as in the storage. This may have been due to the high rainfall during the crop development period, because crop remains in the field during monsoon. But this variety 'Palampur Delight' performed better than its parent and many other gladiolus varieties such as 'Hunting Song', 'Fidelio', 'Her Majesty', 'Oscar', 'Red Beauty', etc., in this region in disease incidence.

This hybrid 'Palampur Delight' produces 1.83 corm and profuse cormels 96 per plant, which represents improved multiplication rate compared to previously known varieties.

As in gladiolus plants, the diameter of flowers and ruffledness of petals are considered for its classification, the Applicants have given the same while describing the shape and dimensions of the petals.

The hybrid was raised through conventional method of breeding. Seeds produced by hybridization of different parents were sown in the field to raise hybrid plants. After considering quality parameters some of the promising plants were selected for further multiplication. In the second year onwards, selected hybrids were multiplied and maintained vegetatively by corm and cormels. After hybridization, the hybrids are multiplied vegetatively since 1992.

The colour specifications of the flower parts distinguishing 'Palampur Delight' from others within the same botanical and market class have been incorporated according to R.H.S. Colour Chart published by The Royal Horticultural Society, 80 Vincent Square, London S W1P 2PE, 1995. R.H.S. Color chart is an internationally accepted color chart for identifying/referring colors of plants or plant parts. The distinguishing characteristics are compared with other varieties of same botanical and market class emphasize the distinctiveness of 'Palampur Delight'.

The hybrid is a cross between two gladiolus varieties, 'Her Majesty', and 'Eurovision'. Both 'Her Majesty' and 'Eurovision' are of the genus Gladiolus L and species Gladiolus sp. (Gladiolus Hybrid). Neither of the parent varieties are patented. 'Her Majesty' was used as female and 'Eurovision' as male to create the hybrid 'Palampur Delight'. 'Palampur Delight' is distinct from its parents. For example, 'Her Majesty' has ruffled petals, Blue Violet in color with darker edges and a white throat. 'Eurovision' has flowers that are Light Vermilion colour, with white veins. In contrast, 'Palampur Delight' has bi-colour, Rose Purple (RHS-75 D) flowers with Fuchsia Purple (RHS-67 A) tinge on petals edges. Its lip petal Greenish White (RHS-157 D).

The genotype IHBT-GH-164 ('Palampur Delight') was bred at the Institute of Himalayan Bioresource Technology (IHBT) under the programme of development of new varieties of gladiolus.

The present invention includes the novel and distinct gladiolus plant christened as 'Palampur Delight' and characterized by the following combination of characteristics:

(a) The hybrid is a cross between two gladiolus varieties, 'Her Majesty' and 'Eurovision'.

(b) The hybrid having Standard type of flowers.

(c) The hybrid having bi-colour flowers of Rose Purple (RHS-75D) with Fuchsia Purple (RHS-67A) colour at the edges of the petals. Lip petal Greenish White.

(d) The hybrid having thick and ruffled petals.

(e) The hybrid takes 84 days to flower.

(f) The average number of flower spikes/plant is 1.68.

(g) The average length of flower spikes is 125 cm.

(h) The average number of flowers per spikes is 16.4.

Gladiolus varieties 'The Saint', 'Grace', and 'Palampur Pride' are described in copending patent applications with Ser. Nos. 10/106,085, 10/106,301, and 10/106,300, respectively, each of which is incorporated herein by reference. These varieties differ from 'Palampur Delight' in numerous aspects including flower color. 'The Saint' has Shrimp Red (RHS-33C) flowers with Vermilion (RHS-41A) colour on center of the lip petals. 'Grace' has Salmon (RHS-27B) flowers with Poppy Red (RHS-40D) colour on petal edges and Chartreuse Yellow (RHS-2) on lip petal. 'Palampur Pride' has Primerose Yellow (RHS-4 ) flowers with Fuchsia Purple (RHS-67 A) tinge on petals edges and a lip petal that is Barium Yellow (RHS-10 C) with magenta (RHS-66 C) lines. These several varieties differ in numerous other characteristics. The different characteristics can readily be determined by reading each of the plant applications.

What is claimed is:

1. A new and distinct gladiolus plant called 'Palampur Delight' and substantially as shown and described.

* * * * *

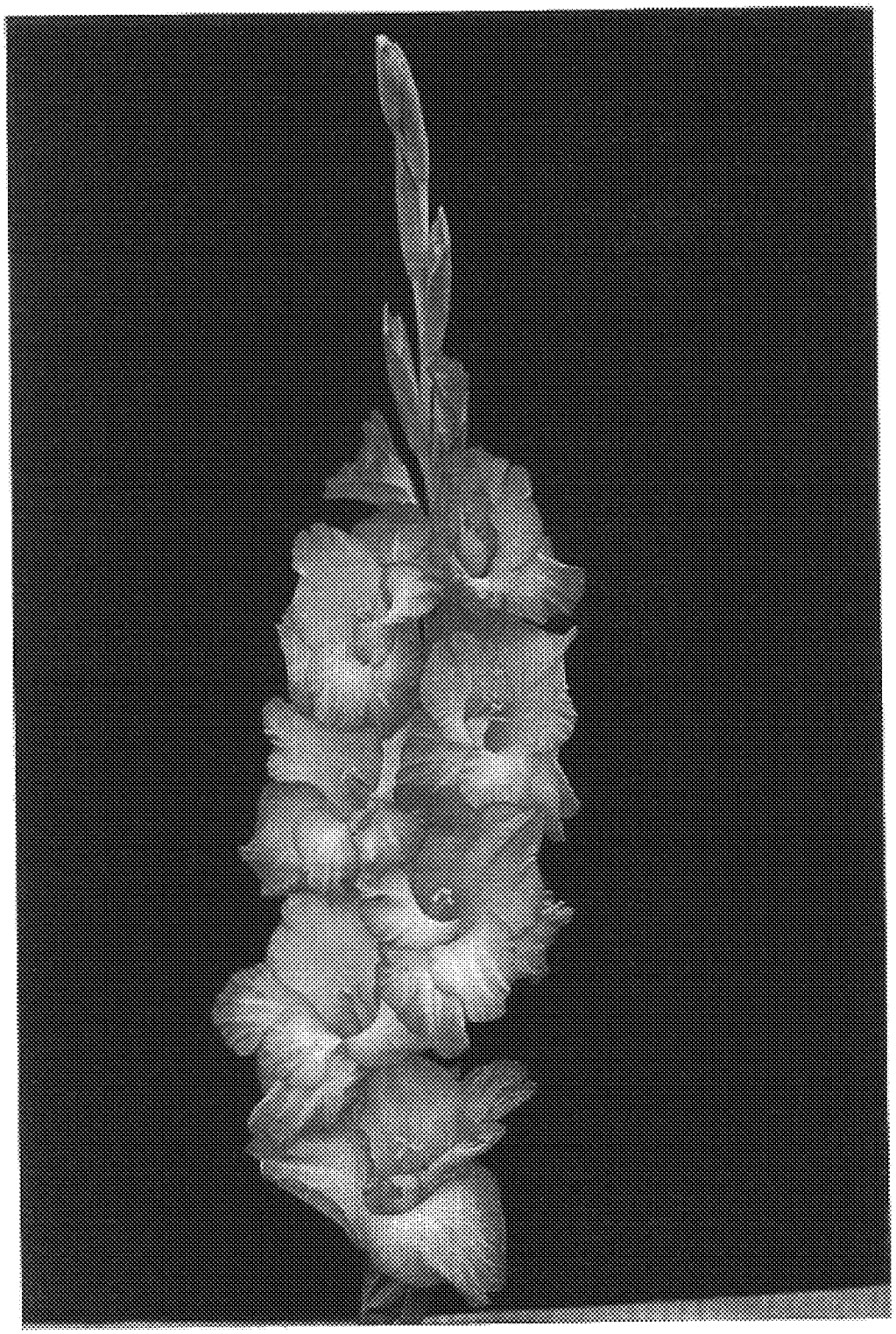
Gladiolus hybrid plant 'PALAMPUR DELIGHT'